United States Patent [19]

Whitney et al.

[11] 4,392,847

[45] Jul. 12, 1983

[54] INJECTION AND MONITORING SYSTEM

[76] Inventors: Douglass G. Whitney, 2518 W. Wesley Rd.; John K. Martin, III, 2837 Ridge Wood Cir., both of Atlanta, Ga. 30327

[21] Appl. No.: 260,964

[22] Filed: May 6, 1981

Related U.S. Application Data

[63] Continuation-in-part of Ser. No. 1,091, Jan. 8, 1979, Pat. No. 4,273,122, and a continuation-in-part of Ser. No. 964,953, Nov. 30, 1978, Pat. No. 4,235,234, which is a continuation-in-part of Ser. No. 741,528, Nov. 12, 1976, Pat. No. 4,150,672.

[51] Int. Cl.³ .............................................. A61M 5/00
[52] U.S. Cl. ........................... 604/118; 128/DIG. 13; 128/655; 604/245
[58] Field of Search ....... 128/214 E, 214 F, DIG. 12, 128/DIG. 13, 213 R, 655; 604/118, 121, 245

[56] References Cited

U.S. PATENT DOCUMENTS

| | | | |
|---|---|---|---|
| 3,091,239 | 5/1963 | Moeller | 128/214 F |
| 3,882,861 | 5/1975 | Kettering et al. | 128/214 E |
| 3,901,231 | 8/1975 | Olson | 128/214 F |
| 4,006,736 | 2/1977 | Kranys et al. | 128/655 |
| 4,150,672 | 4/1979 | Whitney et al. | 128/214 E |
| 4,191,184 | 3/1980 | Carlisle | 128/214 E |
| 4,267,834 | 5/1981 | Barger et al. | 128/214 F |

*Primary Examiner*—Dalton L. Truluck
*Attorney, Agent, or Firm*—B. J. Powell

[57] ABSTRACT

A system for injecting fluid into a patient and monitoring the blood pressure of the patient comprising an injector for incrementally injecting the fluid through a delivery tube into the vascular system of the patient at selected prescribed rates with display means and rate indicator means generating an output indicative of the rate of fluid injection connected to the display means for visually displaying the rate at which the fluid is being injected; a blood pressure monitor including transducer means communicating with the vascular system of the patient through the delivery tube on the injector for providing an output indicative of the patient's blood pressure and pressure detector means responsive to the output of the transducer means to generate an output indicative of the systolic and diastolic blood pressures of the patient; and mounting means for selectively mounting the blood pressure monitor on the injector and including connector means connecting the output of the pressure detector means in the blood pressure monitor to the display means in the injector when the blood pressure is mounted on the injector for visually displaying the patient's systolic and diastolic blood pressure on the display means. Disabling means is provided for disabling the pressure detector means when the fluid is incrementally injected by the injector to prevent errors in the indicated blood pressure. The connector means also connects a battery in the injector to the monitor to power same.

9 Claims, 6 Drawing Figures

INJECTION AND MONITORING SYSTEM

CROSS-REFERENCE TO RELATED APPLICATIONS

This application is a continuation-in-part of our copending application Ser. No. 1,091, filed Jan. 8, 1979, now U.S. Pat. No. 4,273,122, and a continuation-in-part of our earlier applications Ser. No. 964,953, filed Nov. 30, 1978, now U.S. Pat. No. 4,235,234, which is a continuation-in-part of Ser. No. 741,528, filed Nov. 12, 1976, now U.S. Pat. No. 4,150,672.

BACKGROUND OF THE INVENTION

This invention relates generally to monitoring and injection systems and more particularly to an injection system which has the capability to monitor the blood pressure of a patient.

Blood pressure monitoring systems are available to monitor the blood pressure of a patient. These systems typically monitor the systolic, diastolic, and/or mean blood pressure of a patient. Such systems typically use a transducer which is connected to the vascular system of the patient so that the transducer is exposed to the patient's blood pressure. The output of the transducer is typically connected to a detection circuit for detecting the systolic, diastolic, and/or mean blood pressure of the patient and is appropriately connected to a display for displaying one or more of these pressures. These systems also require a fluid drip system to keep the line connecting the transducer to the vascular system of the patient open.

Similarly, injection systems are available for injecting a treatment fluid into the patient over a prolonged period of time. Typically, such injections are made intravenously into the patient's vascular system.

It is also frequently desirable to monitor the patient's blood pressure while such injections are being made into the patient's vascular system. Heretofore, it was necessary to connect the injection system at one point in the patient's vascular system so that the fluid could be injected and to connect the blood pressure monitoring system at another position in the patient's vascular system so that the blood pressure monitoring system was isolated from the injection system.

Further, prior art blood pressure monitoring systems which make direct blood pressure measurements through the use of arterial catheters have normally required a hospital setting. This is because the equipment used in such prior art monitoring systems is confining and does not allow the patient to be fully ambulatory.

SUMMARY OF THE INVENTION

These and other problems and disadvantages associated with the prior art are overcome by providing a system which has the capability of injecting fluid into a patient and monitoring the blood pressure of the patient at the same time. The blood pressure monitor is mounted on the injector and uses the same connection used by the injector to expose the blood pressure monitor to the patient's blood pressure for monitoring. The blood pressure monitor can be selectively mounted on the injector so that the injector can be used to inject fluid into the patient without blood pressure monitoring or with blood pressure monitoring when the blood pressure monitor is mounted on the injector. The system includes means for disabling the blood pressure monitor while the injector is injecting fluid into the patient so that the monitored blood pressure reading from the patient is not distorted by the injection of the fluid into the patient. Further, the display normally used to display the injection rate at which the fluid is being injected on the injector is used to display the patient's blood pressure when the blood pressure monitor is operatively mounted on the injector to minimize the components used in the system. The blood pressure monitor is also powered through the power supply carried by the injector to further minimize the components used in the system.

By minimizing the components used in the system, the system is reduced to a size which permits its mounting on the patient's arm in the vicinity of the connection of the system to the vascular system of the patient. This has the advantage of the patient remaining ambulatory and also minimizing recalibration of the system each time the patient changes position. At the same time, the requirement of a separate fluid drip system to keep the transducer line open is eliminated since the injector performs this function. Further, the injector of the system provides the capability of administering a fluid medicament as required in addition to keeping the transducer line open.

The system of the invention includes an injector carrying the fluid to be injected into the patient with a delivery tube from the injector connected to the vascular system of the patient so that the fluid can be injected into the patient. The injector includes an expelling means for incrementally injecting the fluid through the delivery tube into the patient at selected prescribed rates, rate indicator means for generating an output indicative of the rate of fluid injection and display means connected to the output of the indicator means for visually displaying the rate at which the fluid is being injected. The system also includes a blood pressure monitor with transducer means connectable to the delivery tube on the injector to place the transducer in communication with the patient's vascular system where the transducer means provides an output indicative of the patient's blood pressure. A pressure detector means responsive to the output of the transducer means generates output indicative of the systolic and diastolic blood pressures of the patient. The system also includes mounting means for selectively mounting the transducer means on the injector where the mounting means causes the outputs of the pressure detector means to be connected to the display means and to cause the output of the rate indicator means to be disconnected from the display means so that the display means visually displays the patient's systolic and diastolic blood pressures when the mounting means mounts the transducer on the injector.

These and other features and advantages of the invention disclosed herein will become more apparent upon consideration of the following specification and accompanying drawings wherein like characters of reference designate corresponding parts throughout the several views and in which:

These figures and the following detailed description disclose specific embodiments of the invention; however, it is to be understood that the inventive concept is not limited thereto since it may be embodied in other forms.

DETAILED DESCRIPTION OF ILLUSTRATIVE EMBODIMENTS

Figure 1:
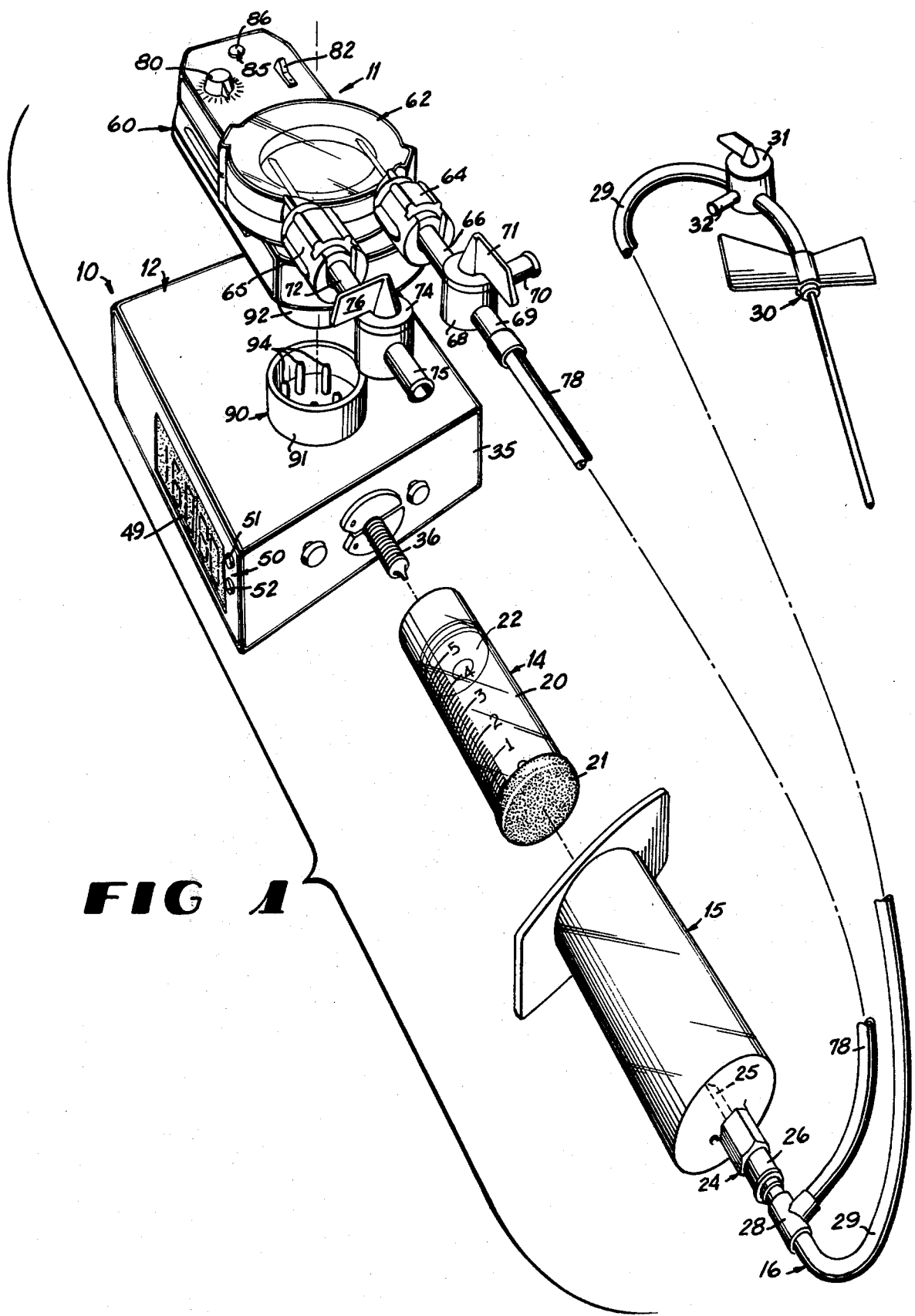
FIG. 1 is an exploded perspective view illustrating the system of the invention.

Referring to FIG. 1, it will be seen that the system of the invention includes generally an injector 10 and a blood pressure monitor 11. The injector 10 is of the type disclosed in our co-pending application Ser. No. 1,091. The injector 10 serves to incrementally inject liquid medicament into the vascular system of the patient at a prescribed programmed rate. The monitor 11 is mounted on the injector 10 and serves to monitor the patient's blood pressure. The monitor 11 operates in conjunction with the injector 10 and utilizes certain components of the injector 10 in its operation.

The injector 10 includes generally a power unit 12 which selectively mounts an ampule 14 thereon with an ampule holder 15. A connector assembly 16 is used to connect the ampule with the patient so that the fluid carried in the ampule 14 can be forced therefrom into the patient via the connector assembly 16 by the power unit 12.

The ampule 14 has a tubular side wall 20 closed at one end by a penetrable rubber plug 21 with a resilient expelling piston 22 slidably received in the other end of the side wall 20. The liquid medicament to be dispensed is carried in the ampule 14 between the plug 21 and piston 22. To provide a fluid outlet through the penetrable rubber plug 21, a piercing assembly 24 is mounted in the ampule holder 15 so that the piercing needle 25 thereon penetrates the plug 21 as the ampule holder 15 positions the ampule 14 on the power unit 12. Thus, as the piston 22 is moved toward the plug 21, the liquid medicament will be forced out of the ampule 14 through the piercing assembly 24. Typically, the piercing assembly 24 includes a check valve 26 which permits the fluid to flow out of ampule 14 but prevents fluid from flowing into the ampule 14 through the piercing assembly 24.

The piercing assembly 24 is connected to the patient via connector assembly 16. Connector assembly 16 includes a T-shaped connector 28 with one of its inlets connected to the outlet of check valve 26. A delivery tube 29 connects the outlet of connector 28 with an intravenous injection assembly 30 through a valve 31. The injection assembly 30 permits connection to the vascular system of the patient in known manner. The other inlet to the connector 28 is closed when the blood pressure monitoring system 11 is not being used so that fluid forced out of the ampule 14 by the piston 22 will be directed through the connector assembly 16 into the vascular system of the patient.

The power unit 12 includes a housing 35 which mounts the ampule 14 and holder 15 thereon. A drive screw 36 is mounted in housing 35 and projects into the ampule 14 to engage the piston 22 in ampule 14. The drive screw 36 is adapted to be axially moved with respect to the ampule 14 by an electrically operated drive means 38 schematically seen in FIG. 2 to engage the piston 22 and move it toward the plug 21 to selectively force the liquid medicament from ampule 14 into the patient. The drive means 38 may be a solenoid or stepping motor such as that disclosed in our co-pending application Ser. No. 1,091.

Figure 2:
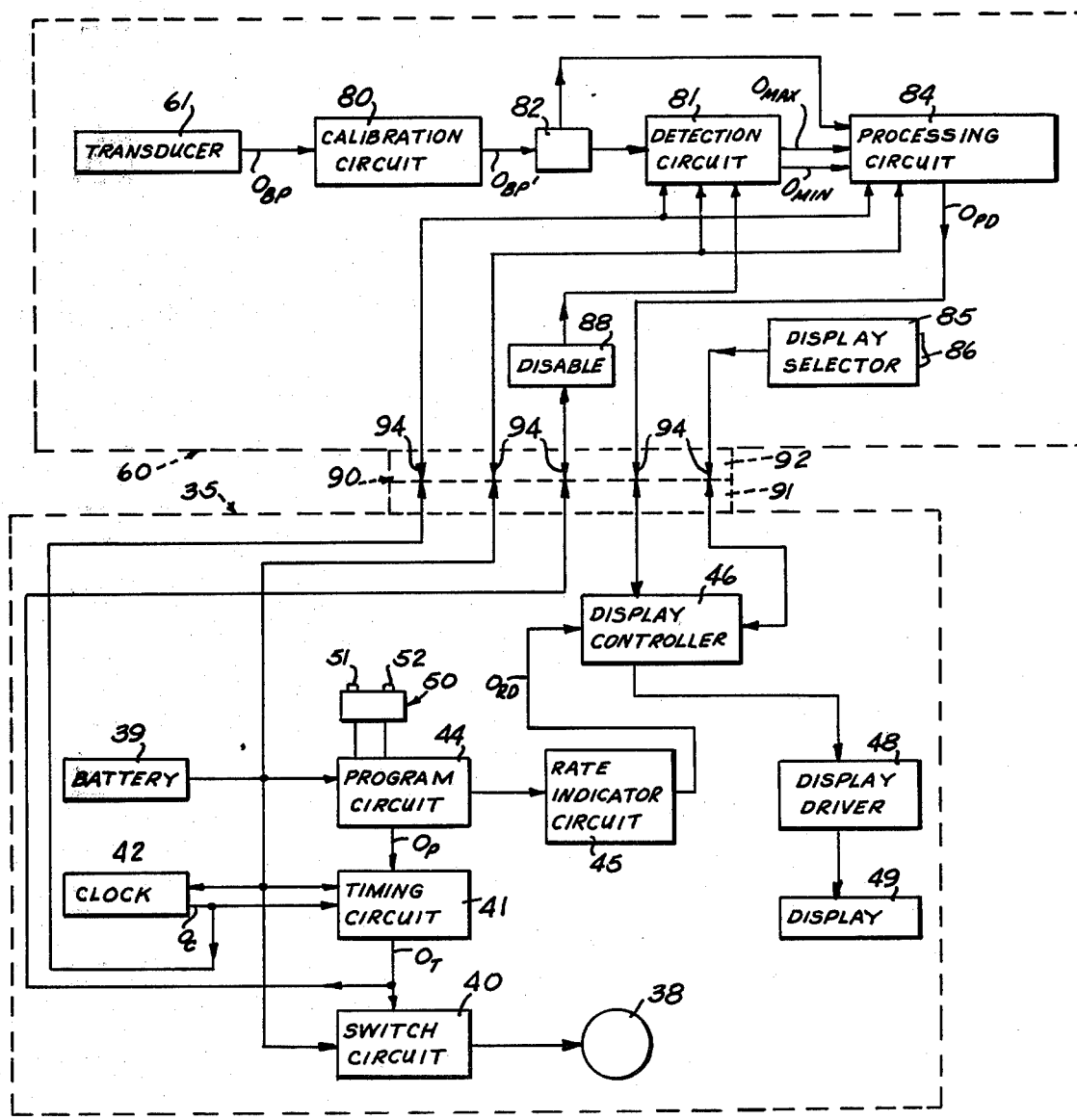
FIG. 2 is a functional block diagram of a system in accordance with the teachings of the invention.

Also housed in housing 35 and schematically shown in FIG. 2 is a battery 39 to supply power to the power unit 12 and a switching circuit 40 for selectively connecting the battery 39 to the driving means 38 to cause the driving means 38 to move drive screw 36 and expel fluid from ampule 14. The housing 35 also carries a timing circuit 41 for controlling switching circuit 40, a clock 42 for providing a reference input to the timing circuit 41, a program circuit 44 for controlling the timing circuit 41, a rate indicator circuit 45, a display control circuit 46, a display driver 48 and a liquid crystal digital display 49. These components are schematically shown in FIG. 2.

The timing circuit 41 generates a pulsed output $O_T$ which causes the switching circuit 40 to alternatively connect and disconnect the drive means 38 to the battery 39. Each time the switching circuit 40 connects the drive means 38 to battery 39, the drive means moves the piston 22 toward the plug 21 in ampule 14 so that a prescribed amount of the liquid medicament is injected into the patient. Likewise, when the drive means 38 is disconnected from the battery 39, the piston 22 is stopped. Thus, the average rate at which the liquid medicament is injected is the volume of liquid medicament injected while drive means 38 is connected to battery 39 divided by the sum of the time the drive means 38 is connected to battery 39 and the time the drive means 38 is disconnected from battery 39. Thus, controlling the pulsed output $O_T$ of timing circuit 41 serves to control the rate at which the liquid medicament is injected.

The clock 42 provides a pulsed reference output $O_C$ to the timing circuit 41. The reference output $O_C$ remains the same and the timing circuit 41 generates its output $O_T$ based on a selected number of pulses having been received in the reference output $O_C$. The program circuit 44 has a programming output $O_P$ connected to the timing circuit 41 which serves to adjust the timing circuit 41 so that its output $O_T$ can be based on different numbers of selected pulses having been received in the reference output $O_C$. The program circuit 44 is controlled by a manual input switch network 50 to adjust the programming output $O_P$ thereof so that the desired rate of fluid injection can be controlled. The program circuit 44 also generates a rate output $O_R$ indicative of the rate of liquid medicament injection to which the program circuit 44 has been adjusted. The rate output $O_R$ is connected to the rate indicator circuit 51 which processes the output $O_R$ into a rate display output $O_{RD}$ supplied to the display driver 48 through the display control circuit 46. The display driver 48 causes the rate of injection of the liquid medicament to be displayed by the display 49.

The program circuit 44 has a programming mode in which the injection rate can be changed and an operating mode in which the injection rate cannot be changed. In the programming mode, the programming output $O_P$ is not generated and the timing circuit 41 is disabled so that the switching circuit 40 is also disabled and battery 39 is not connected to the drive means 38. When the program circuit 44 is in the operating mode, the pregramming output $O_P$ is generated and timing circuit 41 is operated to cause the switching circuit 40 to alternatively connect and disconnect the drive means 38 to battery 39 and inject the liquid medicament at the rate programmed into the program circuit 44.

The manual input switch network 50 includes an operating mode switch 51 and a program mode switch 52. When the operating mode switch 51 is manually manipulated, this causes the program circuit 44 to shift into its operating mode and the output $O_P$ therefrom to be generated to cause the liquid medicament to be injected at the rate to which the program circuit 44 is adjusted when it shifts to the operating mode. When the program mode switch 52 is manipulated while the program circuit 44 is in its operating mode, the program circuit 44 will initially be shifted into its program mode. As the operator continues to close switch 52, the program circuit 44 will be adjusted to increase the programmed rate of injection. The longer the operator closes switch 52, the faster the programmed rate of injection will be increased. If the operator releases and then recloses the switch 52, the program circuit 44 will be adjusted to decrease the programmed rate of injection. The longer the operator closes switch 52, the faster the programmed rate of injection will be decreased. If the operator again releases and then recloses the switch 52, the program circuit 44 will again be adjusted to increase the programmed rate of injection. Thus, the switch 52 allows the operator to adjust the programmed rate of injection to be adjusted to the desired programmed rate of injection.

Figure 3A:
FIGS. 3a and 3b illustrate the values displayed by the system of the invention.

The program circuit 44 generates the rate output $O_R$ while it is in the program and operating modes. Thus, as the operator adjusts the rate of injection of the program circuit 44, the programmed rate of injection is displayed on the display 49 so that the operator can visually determine what the programmed rate of injection is as it is being adjusted. When the desired rate of injection has been programmed into the program circuit 44, the operator closes the operating mode switch 51 to cause the program circuit 44 to shift into its operating mode. This causes the output $O_P$ to be generated and timing circuit 41 to be enabled to inject the liquid medicament at the rate to which the program circuit 44 has been programmed. The display 49 continues to display the rate at which the liquid medicament is being injected. FIG. 3(A) illustrates the display 49 displaying an injection rate in cubic centimeters per twenty-four hours. The rate indicator circuit 45 may be appropriately constructed to cause the injection rate to be displayed in other values such as units of liquid medicament and/or for other time periods.

The blood pressure monitoring system 11 includes a housing 60 seen in FIG. 1 which mounts a pressure transducer 61 schematically seen in FIG. 2. The pressure transducer 61 is of the piezoelectric type well known in the art which generates an output indicative of the pressure imposed thereon. A pressure dome 62 is connected to the housing 60 over the transducer 61 to place the patient's vascular system in operative association with the transducer 61 so that the patient's blood pressure is imposed on transducer 61. The pressure dome 62 has a fluid cavity therein with a thin membrane between the cavity and the transducer 61 so that the pressure of the fluid in the cavity will be transmitted to transducer 61 to vary its output. The pressure dome 62 has an inlet 64 and an outlet 65.

The inlet 64 is connected to the tube 66 on multi-position inlet valve 68 while the outlet 65 is connected to the tube 72 on a two-position outlet valve 74. The tube 69 on the valve 68 is connected to the other inlet on connector 28 in the connector assembly 16 through an input tube 78. The other tube 70 on valve 68 is left open as will become more apparent. Valve 68 is provided with a control lever 71 which can be manipulated to selectively connect tubes 66 and 69 or tubes 66 and 70 or tubes 69 and 70. In the position shown, tubes 66 and 69 are connected. The tube 75 on valve 74 is left open and valve 74 is provided with a control lever 76 which can be manipulated to connect tubes 72 and 75 or to block tube 74 from tube 72. In the position shown, tube 75 is blocked from tube 72. The valves 68 and 74 together with the valve 31 in the connector assembly 16 are used to fill the cavity in pressure dome 62 and input tube 78 with a liquid so that the transducer 61 can be placed in pressure transmitting communication with the liquid in the delivery tube 29.

To fill the cavity in pressure dome 62 and the input tube 78, the tube 70 is connected to a liquid supply. Typically, the liquid is a sterile saline solution. The lever 71 on valve 68 is manipulated to connect tubes 69 and 70. If the injector 10 is already connected to the patient so that tube 29 is already filled, the operator fills the input tube 78 with the liquid from the liquid supply while it is disconnected from connector 28 and then connects it to the connector 28. The operator then manipulates the lever 71 on valve 68 to connect tubes 66 and 70 and manipulates lever 76 on valve 74 to connect tubes 72 and 75. The cavity in the pressure dome 62 is then filled with liquid from the liquid supply. After this, the operator manipulates lever 71 on valve 68 to connect tubes 66 and 69 and manipulates lever 76 on valve 74 to block tube 72 from tube 75. The transducer 61 is now ready for calibration as will be explained.

As best seen in FIG. 2, the transducer 61 has its output $O_{BP}$ indicative of the pressure thereon connected to a calibration circuit 80. The calibration circuit 80 serves to adjust the output from transducer 61 against a zero base value as will become more apparent and generates a calibrated output $O_{BP}'$ to a detection circuit 81 through a mode select switch 82. The detector circuit 81 operates to detect the maximum and minimum values of the pressure indicated by the calibrated output $O_{BP}'$ from the calibration circuit 80 within a prescribed time period and generates outputs $O_{MIN}$ and $O_{MAX}$ respectively indicative of the minimum and maximum values of the output $O_{BP}'$. The outputs $O_{MIN}$ and $O_{MAX}$ are connected to a processing circuit 84 which processes the outputs $O_{MIN}$ and $O_{MAX}$ into a pressure display output $O_{PD}$ suitable for display on the display 49 to visually indicate the maximum and minimum values of the calibrated output $O_{BP}'$.

The mode select switch 82 has an operating output line $L_O$ connected to the detection circuit 81 and a calibration output line $L_C$ connected to the processing circuit 84. The mode select switch 82 can be manipulated to connect the output $O_{BP}'$ to the line $L_O$ to detector circuit 81 to place the monitor 11 in an operating mode or to connect the output $O_{BP}'$ to the line $L_C$ to processing circuit 84 to place the monitor 11 in a calibration mode. Thus, when monitor 11 is in its calibration mode, the output $O_{BP}'$ is disconnected from detection circuit 81 and connected to processing circuit 84. In this mode, the processing circuit 84 processes output $O_{BP}'$ into an output suitable for display on display 49 as will become more apparent. When the monitor 11 is in the operating mode, the output $O_{BP}'$ is disconnected from the processing circuit 84 and connected to detection circuit 81 to detect the maximum and minimum values in output $O_{BP}'$.

A mounting means 90 is provided for mounting the housing 60 of the blood pressure monitor 11 on the housing 35 of the injector 10 as seen in FIG. 1. The mounting means 90 also serves to electrically interconnect the injector 10 and blood pressure monitor 11. While the mounting means 90 may have different configurations, it is illustrated as a two-piece connector with one connector half 91 mounted on housing 35 and the other connector half 92 mounted on housing 60. The connector halves 91 and 92 have a plurality of mating contacts 94 that electrically interconnect with each other when the connector halves 91 and 92 are interconnected.

As seen in FIG. 2, one set of contacts 94 connects the battery 39 to the detection circuit 81 and processing circuit 84 to power them. This eliminates the need of having a separate power supply in monitor 11. Another set of contacts 94 connects the reference output $O_C$ from clock 42 to the detection circuit 81 to provide a timing reference to detection circuit 81 and establish the time period over which the detection circuit 81 detects the maximum and minimum pressure values in the calibrated output $O_{BP}'$. This eliminates the need of having a separate clock in the monitor 11. Another set of contacts 94 connects the output $O_{PD}$ from the processing network 84 to the display controller 46. Another set of contacts 94 connects a display selector 85 in the monitor 11 with the display controller 46. When the monitor 11 is not mounted on injector 10 so that the display selector 85 is disconnected from the display controller 46, the display controller 46 connects the output $O_{RD}$ from the rate indicator circuit 45 to the display driver 48 so that the injection rate of the liquid medicament is displayed on display 49. When the monitor 11 is mounted in the injector 10 to connect the display selector 85 to display controller 46, the display controller 46 disconnects output $O_{RD}$ from the display driver 48 and connects the output $O_{PD}$ from the processing circuit 84 to the display driver 48 so that the output $O_{PD}$ will be displayed on display 49. The display selector 85 is provided with an appropriate switch 86 which, when depressed by the operator to close it, causes the display controller 46 to disconnect the output $O_{PD}$ from the display driver 48 and reconnect the output $O_{RD}$ from the rate indicator circuit 45 to display driver 48 to display the injection rate on display 49 as long as switch 86 is depressed. This eliminates the need for a separate display to display the output of the monitor 11.

As will become more apparent, another set of contacts 94 in the mounting means 90 connects the output $O_T$ from the timing circuit 41 to a disable circuit 88 in the monitor 11. The disable circuit 88 is in turn connected to the detection circuit 81. The disable circuit 88 serves to disable the detection circuit 81 each time the output $O_T$ from timing circuit 41 causes the switching circuit 40 to connect battery 39 to the drive means 38 and maintains the detection circuit 81 disabled for a sufficient period of time to permit the pressure increase in the delivery tube 29 due to the injection of the liquid medicament to dissipate before again enabling the detection circuit 81. This serves to prevent the pressure generated during liquid medicament injection from affecting the outputs $O_{MIN}$ and $O_{MAX}$ from the detection circuit 81 as will become more apparent.

It will be appreciated that connection of the monitor 11 to the injector 10 does not affect the injection of the liquid medicament by the injector 10. Even though the injection rate is not displayed unless the display selector switch 86 is depressed, the injector 10 continues the injection operation in its usual manner.

When the monitor 11 is mounted on the injector 10, and the pressure dome 62 and input tube 78 filled with liquid as described above, the monitor 11 is ready for calibration. The lever 71 on inlet valve 68 is manipulated to block the tube 66, and the lever 76 on outlet valve 74 is manipulated to connect tubes 72 and 75 and expose the fluid in the pressure dome 62 to the atmosphere. The mode select switch 82 is manipulated to place the monitor 11 in a calibration mode. This connects the output $O_{BP}'$ to the processing circuit 84 so that its output $O_{PD}$ corresponds to output $O_{BP}'$ and is displayed on display 49. The calibration circuit 80 is then adjusted using the manual control 80' thereon until the output $O_{BP}'$ is zeroed as indicated on the display 49. This serves to adjust the output $O_{BP}$ from the transducer 61 so that the calibrated output $O_{BP}'$ will be indicative of the actual blood pressure imposed on the transducer 61 as is well known in the art.

After calibration, the operator manipulates lever 76 on valve 74 to block tube 72 and manipulates lever 71 on valve 68 to connect tubes 66 and 69. This serves to impose the pressure in the fluid in input tube 78 on the transducer 61. The operator also manipulates the mode select switch 82 to place monitor 11 in an operating mode with the output $O_{BP}'$ connected to the detection circuit 81.

Because the injection assembly 30 is connected to the vascular system of the patient, the patient's blood pressure will be transmitted to the transducer 61 via the liquid in the delivery tube 29, the input tube 78 and the cavity of the pressure dome 62. This causes the output $O_{BP}$ from transducer 61 to be responsive to the patient's blood pressure. Because the cavity in the pressure dome 62 is closed to the atmosphere, the fluid in the input tube 78 and pressure dome 62 remains in place and is not injected into the patient. Because the injector 10 is injecting the liquid medicament through injection assembly 30, the injection assembly 30 will remain open to keep the transducer 61 exposed to the patient's blood pressure.

Figure 3B:
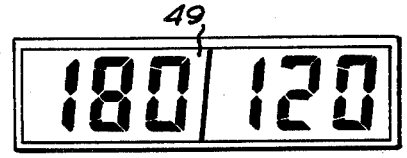

The calibration circuit 80 adjusts this output so that the output $O_{BP}'$ is indicative of the actual blood pressure of the patient. The detection circuit senses the maximum and minimum values of the output $O_{BP}'$ over the period of time selected from the reference output $O_C$ from clock 42 to generate the outputs $O_{MIN}$ and $O_{MAX}$. Thus, it will be seen that the output $O_{MAX}$ indicates the systolic blood pressure of the patient while the output $O_{MIN}$ indicates the diastolic blood pressure of the patient. The processing circuit 84 processes these outputs and generates output $O_{PD}$ to the display driver 48 so that the systolic and diastolic blood pressures of the patient are displayed by display 49 as illustrated in FIG. 3(B).

Figure 4:
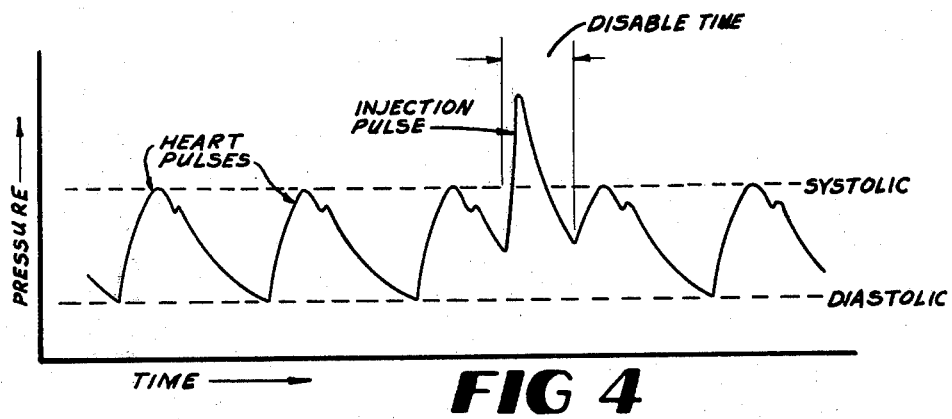
FIG. 4 is a graph illustrating the variations in normal blood pressure and the injection pressure associated with the invention.

It will be appreciated that, when the injector 10 is injecting liquid medicament through the delivery tube 29 into the patient, the pressure within tube 29 will be raised. This increase in pressure will be transmitted to the transducer 61 so that the output $O_{BP}$ thereof will be indicative of this pressure rather than the blood pressure of the patient. To prevent this from affecting the outputs $O_{MIN}$ and $O_{MAX}$ of the detection circuit 81 to give erroneous blood pressure readings, the disable circuit 88 disables the detection circuit 81 each time the timing circuit 41 causes the switching circuit 40 to connect the battery 39 to drive means 38. The disable circuit 88 maintains the detection circuit 81 disabled until the pressure generated in the delivery tube 29 due to the liquid medicament being injected has dissipated. This will be better appreciated by reference to FIG. 4 which shows a typical blood pressure curve in which the injection pressure pulses have been incorporated. It will be seen that the injection pressure pulse is of short duration. Because of this, the detection circuit 81 has a sufficient amount of time to adequately sample the heart pulses to monitor the systolic and diastolic blood pressures of the patient without the injection pressure pulses affecting the blood pressure indications displayed on display 49.

When the operator wants to check the injection rate, the switch 86 to the display selector 85 is depressed to cause the display controller 46 to disconnect the blood pressure output $O_{PD}$ from the display driver 48 and connect the injection rate output $O_{RD}$ to display driver 48. This causes the injection rate to be displayed by display 49 as seen in FIG. 3(A).

If the operator wants to remove a blood sample, the valve 31 may be manipulated to block the liquid in the delivery tube 29 and connect the injection assembly 30 to a side port 32 on valve 31. This allows blood to be withdrawn through the injection assembly 30 and side port 32 in known manner. After the blood is withdrawn, the valve 31 is manipulated to reconnect the liquid in delivery tube 29 to injection assembly 30 to continue the operation of the injector 10 and monitor 11. The delivery tube 29 and the input tube 78 can also be flushed through valve 31 by manipulating valve 31 so that the delivery tube 29 is connected to the side port 32 on valve 31 while the injection assembly 30 is blocked thereby.

Figure 5:
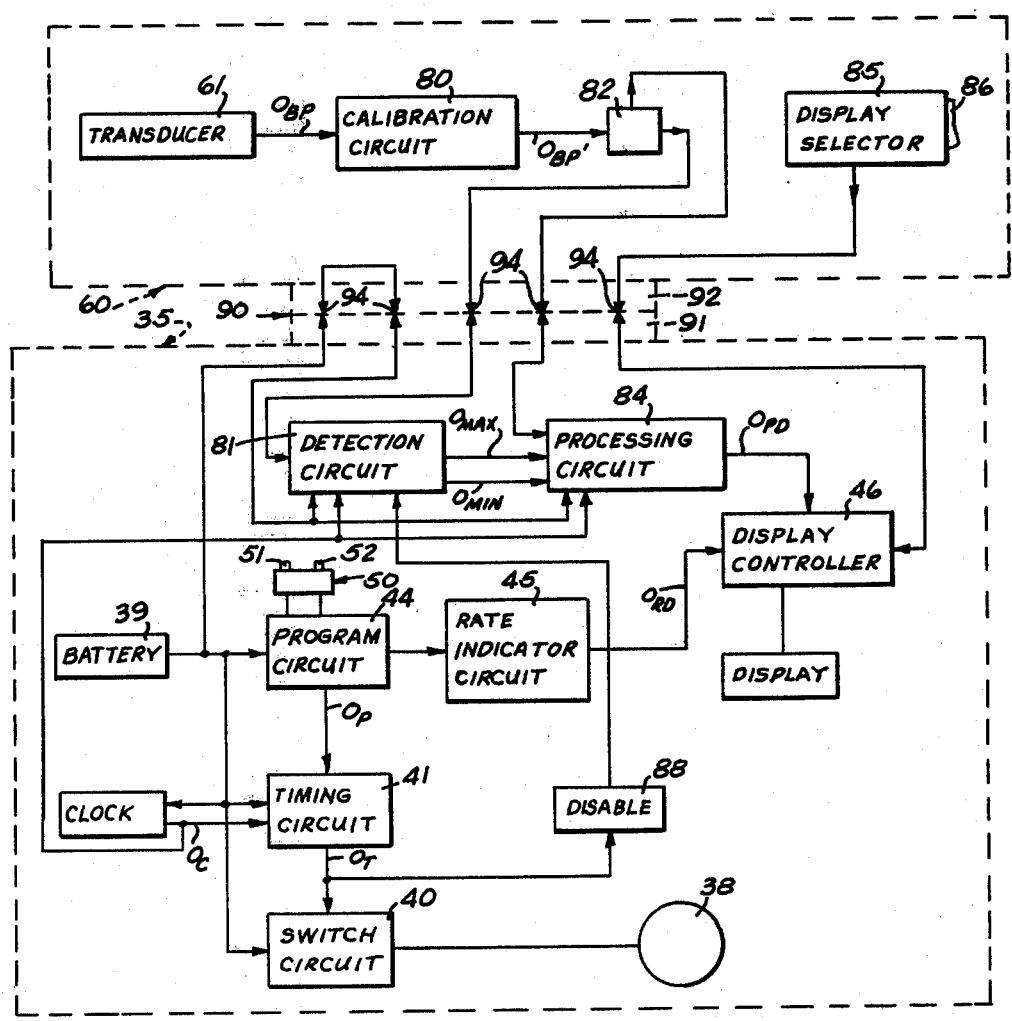
FIG. 5 is a functional block diagram of a further embodiment of the invention.

Because the monitor 11 is operated from the injector 10, some of the components used for the monitor 11 may be incorporated in the injector housing 35. FIG. 5 schematically illustrates such an arrangement.

As seen in FIG. 5, the detection circuit 81, processing circuit 84 and disable circuit 88 are housed in the injector housing 35 while the transducer 61, calibration circuit 80, mode select switch 82 and selector 85 are housed in the monitor housing 60. When the connector halves 91 and 92 are plugged together, one set of contacts 94 connects the battery 39 with another set of contacts 94 connected to the detection circuit 81 and processing circuit 84 to power them. Thus, it will be seen that, while the detection and processing circuits 81 and 84 are located in the injector housing 35, they will not be powered until the connector halves 91 and 92 are plugged together when transducer 61 is mounted on injector 10. The operating output line $L_O$ from mode select switch 82 is connected to the detection circuit 81 through another set of contacts 94. The calibration output line $L_C$ from mode select switch 82 is connected to the processing circuit 84. The display selector 85 is connected to the display controller 46 through another set of contacts 94.

The reference output $O_C$ from clock 42 is connected directly to the detection circuit 81. The disable circuit 88 is connected directly to the output $O_T$ from timing circuit 41 and is in turn connected to detection circuit 81 to disable the detection circuit 81 during injection of the liquid medicament.

Functionally, it will be seen that the circuit arrangement seen in FIG. 5 is the same as that seen in FIG. 2. When the monitor housing 60 is not mounted on the injector housing 35, the detection and processing circuits 81 and 84 are not powered and thus remain inactive. Because the display selector 85 is not connected to the display controller 46, the injector rate will be displayed on the display 49. Mounting the monitor housing 60 on injector housing 35 serves to connect battery 39 to the detection and processing circuits 81 and 84 to activate them. This also connects the output lines $L_O$ and $L_C$ to the detection circuit 81 and the processing circuit 84 respectively to permit blood pressure monitoring. Also, the display selector 85 is connected to the display controller 46 to cause the blood pressure output $O_{PD}$ to be displayed by the display 49.

What is claimed as invention is:

1. A system for injecting fluid into a patient and monitoring the blood pressure of the patient comprising:

injector means carrying the fluid to be injected, said injector defining a fluid outlet therefrom and including expelling means for alternatively and successively discharging fluid for injection out of said fluid outlet for a first prescribed period of time and stopping the discharge of fluid out of said fluid outlet for a second prescribed period of time, display means, and rate indicator means operatively associated with said expelling means for generating an output indicative of the rate of fluid injection connected to said display means for visually displaying the rate at which the fluid is being injected;

delivery tube means connected to said fluid outlet and adapted to be connected to the vascular system of the patient so that the fluid discharged from said fluid outlet will be injected into the vascular system of the patient;

a blood pressure monitor including transducer means having an inlet connected to said delivery tube means between said fluid outlet on said injector means and the patient so that said transducer means is in communication both with the vascular system of the patient through said delivery tube means and with said fluid outlet from said injector means for providing an output indicative of the pressure in said delivery tube means, said monitor further including pressure detector means responsive to the output of said transducer means to generate outputs indicative of the maximum and minimum pressures within said delivery tube means over a prescribed period of time; and mounting means for selectively and removably mounting said blood pressure monitor on said injector means, said mounting means including connector means constructed and arranged so that, as an incident to the mounting of said monitor on said injector means, said connector means operatively connects the output of said pressure detector means in said blood pressure monitor to said display means in said injector means whereby said display means in said injector means automatically visually displays the output of said pressure detector means which is indicative of the maximum and minimum pressures in said delivery tube means so that, while the discharge of fluid from said fluid outlet in said injector means is stopped, the pressures in said delivery tube means and displayed on said display means is the patient's systolic and diastolic blood pressure.

2. The system of claim 1 further including disabling means operatively connected to said expelling means in said injector means and said pressure detector means in said monitor as an incident to the removable mounting of said monitor on said injector means by said mounting means, said disabling means disabling said pressure detector means while said expelling means is discharging fluid out of said fluid outlet so that the pressures displayed on said display means are the systolic and diastolic blood pressures of the patient.

3. The system of claim 1 wherein said injector means further includes battery means connected to said expelling means to power same and wherein said connector means is further constructed and arranged to automatically and operatively connect said battery means to said detector means as an incident to the removable mounting of said monitor on said injector means so that said battery means powers said detector means when said blood pressure monitor is mounted on said injector means.

4. The system of claim 1 further including
display control means operatively connecting said connector means to said display means so that the output of said pressure detector means is connected to said display means through said display control means, said display control further connecting the output of said rate indicator means to said display means; and
display select means operatively connected to said display control means, said display select means having manual input means to selectively and alternatively cause said display control means to connect the output of said rate indicator means and the output of said pressure detector means to said display means to selectively and alternatively visually display the rate at which the fluid is being injected and the patient's systolic and diastolic blood pressure on said display means.

5. The system of claim 1 wherein said injector means further includes clock means generating a reference output and wherein said connector means is further constructed and arranged to connect the reference output of said clock means to said pressure detector means as an incident to said blood pressure monitor being mounted on said injector means to control the operation of said pressure detector means.

6. The system of claim 2 wherein said injector means further includes battery means operatively connected to said expelling means to power same and wherein said connector means is further constructed and arranged to connect said battery to said detector means to power said detector means as an incident of said blood pressure monitor being mounted on said injector means.

7. A system for injecting fluid into a patient and monitoring the blood pressure of the patient comprising:
injector means carrying the fluid to be injected, said injector defining a fluid outlet therefrom and including expelling means for alternatively and successively discharging fluid for injection out of said fluid outlet for a first prescribed period of time and stopping the discharge of fluid out of said fluid outlet for a second prescribed period of time;
display means;
delivery tube means connected to said fluid outlet and adapted to be connected to the vascular system of the patient so that the fluid discharged from said fluid outlet will be injected into the vascular system of the patient;
a blood pressure monitor including transducer means having an inlet connected to said delivery tube means between said fluid outlet on said injector means and the patient so that said transducer means is in communication both with the vascular system of the patient through said delivery tube means and with said fluid outlet from said injector means for providing an output indicative of the pressure in said delivery tube means, said monitor further including pressure detector means responsive to the output of said transducer means to generate outputs indicative of the maximum and minimum pressures within said delivery tube means over a prescribed period of time, said outputs of said pressure detector means operatively connected to said display means to cause said display means to visually indicate the maximum and minimum pressures in said delivery tube means; and
disabling means operatively connected to said expelling means in said injector means and said pressure detector means in said monitor for disabling said pressure detector means while said expelling means is discharging fluid out of said fluid outlet so that the pressures displayed on said display means are the systolic and diastolic blood pressures of the patient.

8. The system of claim 1 wherein said injector means includes an injector housing; wherein said monitor includes a monitor housing; and wherein said connector means includes a first connector section mounted on said injector housing and a second connector section mounted on said monitor housing, said first and second connector sections removably interconnectable to removably mount said monitor on said injector means.

9. The system of claim 8 wherein said first and second connector sections include mating contacts which electrically connect said pressure detector means with said display means as an incident to the interconnection of said first and second connector sections.

* * * * *